(12) United States Patent
Petterson et al.

(10) Patent No.: US 11,749,403 B2
(45) Date of Patent: *Sep. 5, 2023

(54) DEVICES, SYSTEMS, AND METHODS FOR PHYSIOLOGY MONITORING

(71) Applicant: AliveCor, Inc., Mountain View (CA)

(72) Inventors: Frank Petterson, Los Altos Hills, CA (US); Melissa McLean, Novato, CA (US); Arthur Okamoto, Mountain View, CA (US); James Jenkins, Mountain View, CA (US); Vivek Gundotra, Los Gatos, CA (US); David Albert, Oklahoma City, OK (US)

(73) Assignee: AliveCor, Inc., Mountain View, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/693,024

(22) Filed: Mar. 11, 2022

(65) Prior Publication Data
US 2022/0199251 A1    Jun. 23, 2022

Related U.S. Application Data

(63) Continuation of application No. 16/871,750, filed on May 11, 2020, now Pat. No. 11,276,491, which is a
(Continued)

(51) Int. Cl.
*G08B 21/04*    (2006.01)
*G16H 40/67*    (2018.01)
(Continued)

(52) U.S. Cl.
CPC ............ *G16H 40/67* (2018.01); *G16H 10/20* (2018.01); *G16H 10/60* (2018.01); *G16H 40/63* (2018.01);
(Continued)

(58) Field of Classification Search
USPC ............ 340/539.12, 539.22, 539.24, 539.25, 340/573.1, 573.3, 692, 825.19, 3.63, 5.52,
(Continued)

(56) References Cited

U.S. PATENT DOCUMENTS 8,688,468 B1    4/2014 daCosta et al.
9,124,776 B2 *  9/2015 Woo ......................... H04N 7/18
(Continued)

FOREIGN PATENT DOCUMENTS

CN    104200418 A    12/2014
JP    2007020689 A    2/2007
(Continued)

OTHER PUBLICATIONS

Japan Patent Office, Office Action for Japanese Patent Application No. 2019-531606, dated Jun. 14, 2021.
(Continued)

*Primary Examiner* — Daniel Previl
(74) *Attorney, Agent, or Firm* — Womble Bond Dickinson (US) LLP

(57) ABSTRACT

Described herein are software platforms (or "platforms"), systems, devices, and methods for providing effective healthcare to a patient while increasing the efficiency of the healthcare provider. A platform provides effective healthcare to a patient through, but not limited to, monitoring of the physical parameters and therapeutic objectives of the patient. In addition, a platform is further configured to provide a communication link between a patient and a healthcare provider. The platform may be implemented by a system comprising one or more computing devices that interact with or run one or more applications of the platform.

20 Claims, 14 Drawing Sheets

Related U.S. Application Data continuation of application No. 15/692,831, filed on Aug. 31, 2017, now Pat. No. 10,685,090.

(60) Provisional application No. 62/382,227, filed on Aug. 31, 2016.

(51) Int. Cl.
| | |
|---|---|
| *G16H 50/30* | (2018.01) |
| *G16H 10/60* | (2018.01) |
| *G16H 50/20* | (2018.01) |
| *G16H 10/20* | (2018.01) |
| *G16H 40/63* | (2018.01) |
| *G16H 15/00* | (2018.01) |

(52) U.S. Cl.
CPC .............. *G16H 50/20* (2018.01); *G16H 50/30* (2018.01); *G16H 15/00* (2018.01)

(58) Field of Classification Search
USPC ............................................ 340/5.82, 286.07
See application file for complete search history.

(56) References Cited

U.S. PATENT DOCUMENTS

| | | | | |
|---|---|---|---|---|
| 11,276,491 | B2* | 3/2022 | Petterson | ............... G16H 10/60 |
| 2004/0008219 | A1 | 1/2004 | Sarel | |
| 2006/0015016 | A1* | 1/2006 | Thornton | ............... G16H 20/60 |
| | | | | 600/300 |
| 2006/0089542 | A1* | 4/2006 | Sands | ................. A61B 5/0022 |
| | | | | 600/300 |
| 2008/0161731 | A1 | 7/2008 | Woods et al. | |
| 2010/0022850 | A1 | 1/2010 | McKenna et al. | |
| 2013/0030258 | A1 | 1/2013 | Cheung et al. | |
| 2014/0275851 | A1* | 9/2014 | Amble | ................. A61B 6/032 |
| | | | | 600/509 |
| 2015/0164349 | A1* | 6/2015 | Gopalakrishnan | ........................... |
| | | | | A61B 5/02055 |
| | | | | 600/508 |
| 2015/0302539 | A1* | 10/2015 | Mazar | ................... G08B 21/02 |
| | | | | 705/3 |
| 2016/0287166 | A1 | 10/2016 | Tran | |
| 2016/0378950 | A1 | 12/2016 | Reiner | |
| 2017/0027498 | A1 | 2/2017 | Larson et al. | |
| 2020/0077892 | A1 | 3/2020 | Fran | |
| 2020/0088892 | A1 | 3/2020 | Liu et al. | |

FOREIGN PATENT DOCUMENTS

| | | |
|---|---|---|
| JP | 2012123803 A | 6/2012 |
| JP | 2015506733 A | 3/2015 |
| WO | 02067122 A1 | 8/2002 |
| WO | 2013090731 A1 | 6/2013 |

OTHER PUBLICATIONS

China National Intellectual Property Administration, First Office Action for Chinese Application No. 201780067224.6, dated Jun. 15, 2021.

* cited by examiner

902

908

DEVICES, SYSTEMS, AND METHODS FOR PHYSIOLOGY MONITORING

CROSS-REFERENCE

This application is a continuation of U.S. patent application Ser. No. 16/871,750, filed May 11, 2020, and titled "DEVICES, SYSTEMS, AND METHODS FOR PHYSIOLOGY MONITORING", which is a continuation of U.S. patent application Ser. No. 15/692,831, filed Aug. 31, 2017, and titled "DEVICES, SYSTEMS, AND METHODS FOR PHYSIOLOGY MONITORING", now U.S. Pat. No. 10,685,090, which claims the benefit of U.S. Provisional Application No. 62/382,227, filed Aug. 31, 2016, and titled "SOFTWARE APPLICATIONS, SYSTEMS, AND METHODS FOR PHYSIOLOGY MONITORING DEVICES". The disclosures of these applications are herein incorporated by reference in their entirety.

BACKGROUND

The use of smartphones, tablet computers, wearable computers, and "smart" accessories is becoming increasingly prevalent. Smartphones are almost ubiquitous in high income countries and are increasingly popular in middle and low income countries as the costs of production decrease and Internet access becomes more available. This increased prevalence of computing power and devices offers many opportunities for improved ways of monitoring health and placing health management more in the control of the patient.

Cardiovascular disease is a leading cause of death in the world and is prevalent in the populations of high-income and low-income countries alike. Heart rate measurement, blood pressure measurement, and electrocardiography are widely used techniques for diagnosing the cardiovascular health of a patient.

SUMMARY OF THE DISCLOSURE

Described herein are software, systems, devices, and methods for linking a patient with a healthcare provider for the purpose of providing effective healthcare to the patient while increasing the efficiency of the healthcare provider. Software as described herein, in some embodiments, comprises one or more integrated applications on a single platform that connects a patient with a healthcare provider.

Described herein is a platform comprising: a patient application comprising: a software module for receiving sensed data from a sensor configured to sense a physiologic parameter of a patient; a software module for transmitting one or more of the sensed data and a patient communication to a healthcare provider; a software module for receiving a healthcare provider communication; a healthcare provider application comprising: a software module for receiving one or more of the sensed data and the patient communication; a software module for generating the healthcare provider communication and transmitting the healthcare provider communication to the patient; wherein the healthcare provider communication is automatically generated and transmitted in response to one or more of the sensed data or a patient communication that references the sensed data; wherein the healthcare provider communication references the sensed data; and wherein the healthcare provider communication includes an indicia that the healthcare provider communication was generated by the healthcare provider. In some embodiments, the physical parameter comprises a vital sign of the patient. In some embodiments, the physical parameter comprises a heart sound of the patient. In some embodiments, the patient communication is transmitted around a time that the physical parameter is sensed. In some embodiments, the patient communication comprises an audio recording of the patient. In some embodiments, the patient communication comprises a video recording of the patient. In some embodiments, the patient communication is recorded and transmitted to the healthcare provider application in real-time. In some embodiments, the platform comprises the sensor and wherein the sensor is configured to operably couple with a mobile computing device. In some embodiments, the sensor is integrated with the mobile computing device. In some embodiments, the sensor comprises two ECG electrodes. In some embodiments, the healthcare provider communication comprises a message of encouragement or congratulation that is personalized to the patient. In some embodiments, the indicia comprises one or more of an image of the healthcare provider and a logo associated with the healthcare provider. In some embodiments, the healthcare provider application comprises a database comprising data sensed from a plurality of patients, and the healthcare provider application comprises a software module for organizing and segregating the data for each of the plurality of patents. In some embodiments, the patient application and the healthcare provider application each comprise a software module for real-time video communication between the patient and the healthcare provider. In some embodiments, at least a portion of the patient application is unlocked with an e-prescription that is received. Described herein is a computer implemented method comprising: sensing a physical parameter of a patient with a sensor; transmitting one or more of the physical parameter and a patient communication that references the physical parameter; and transmitting to the patient an automatically generated communication in response to one or more of the physical parameter and the patient communication that is transmitted; wherein the automatically generated communication references one or more of the physical parameter and the communication; and wherein the automatically generated communication includes indicia that it was sent by a healthcare provider. In some embodiments, the physical parameter comprises a vital sign of the patient. In some embodiments, the physical parameter comprises a heart sound of the patient. In some embodiments, the patient communication is transmitted around a time that the physical parameter is sensed. In some embodiments, the patient communication comprises an audio recording of the patient. In some embodiments, the patient communication comprises a video recording of the patient. In some embodiments, the patient communication is recorded and transmitted to the healthcare provider in real-time. In some embodiments, the sensor is configured to operably couple with a mobile computing device. In some embodiments, the sensor is integrated with the mobile computing device. In some embodiments, the sensor comprises two ECG electrodes. In some embodiments, the automatically generated communication comprises a message of encouragement or congratulation that is personalized to the patient. In some embodiments, the indicia comprises one or more of an image of the healthcare provider and a logo associated with the healthcare provider. In some embodiments, the method comprises receiving, by the healthcare provider, data sensed from a plurality of patients, and organizing and segregating the data for each of the plurality of patents using a database. In some embodiments, transmitting a real-time video communication between the patient and the healthcare provider. In some embodiments, the step of sensing the physical parameter requires first receiving an e-prescription from the healthcare provider.

BRIEF DESCRIPTION OF THE DRAWINGS

The novel features of the subject matter disclosed herein are set forth with particularity in the appended claims. A better understanding of the features and advantages of the subject matter disclosed herein will be obtained by reference to the following detailed description that sets forth illustrative embodiments, in which the principles of the subject matter disclosed herein are utilized, and the accompanying drawings of which:

FIG. 2B shows a screenshot of an exemplary interface for sensing an ECG; FIG. 2C shows a screenshot of an exemplary interface for sensing a heart rate of a patient; FIG. 2D shows a screenshot of an exemplary interface for sensing a blood pressure of a patient; FIG. 2E shows a screenshot of an exemplary interface for sensing a weight of a patient

DETAILED DESCRIPTION

Figure 1:
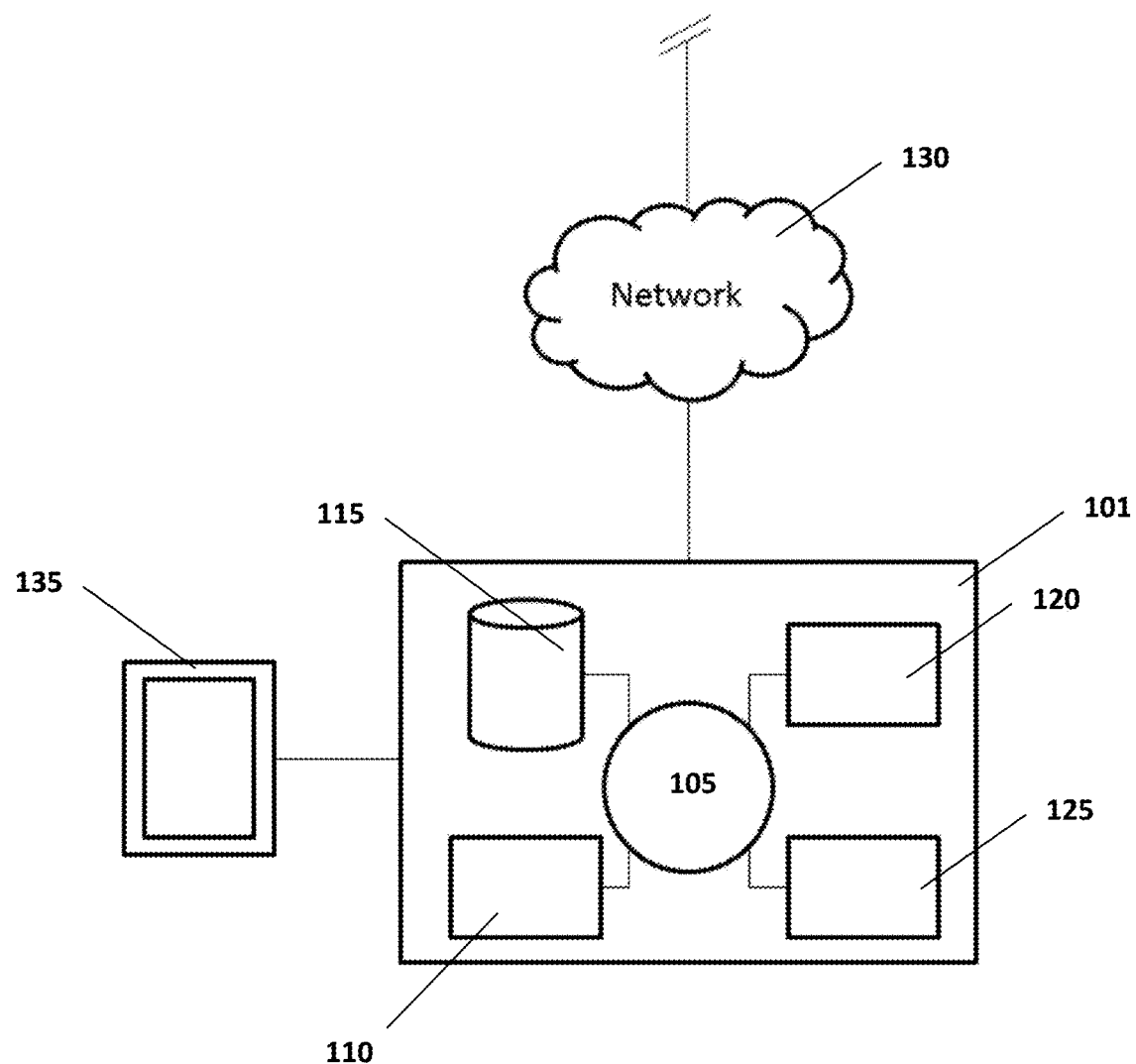
FIG. 1 shows an exemplary embodiment of a platform as described herein comprising a digital processing device.

The term patient" as used herein refers to a human that may use the software platform disclosed herein. None of the terms require or are limited to a situation characterized by the supervision (e.g. constant or intermittent) of a healthcare provider (e.g. a doctor, a registered nurse, a nurse practitioner, a healthcare provider's assistant, an orderly, or a hospice worker).

The terms "sensor" and "sensing device" includes any hardware configured to sense a patient parameter including stand-alone sensors and sensors that include processors or additional computing and/or hardware components (e.g. transmitters or displays).

The term "operably coupled" includes coupling through an operative connection. Such coupling may further comprise a physical integration or a reversible coupling of components. Or, such coupling may be entirely between physically separate components.

Platforms

Described herein are software platforms (or "platforms"), systems, devices, and methods for providing effective healthcare to a patient while increasing the efficiency of the healthcare provider. A platform provides effective healthcare to a patient through, but not limited to, monitoring of the physical parameters and therapeutic objectives of the patient. In addition, a platform is further configured to provide a communication link between a patient and a healthcare provider. The platform is configured so that a patient is provided with more direct and timely access to a healthcare provider while at the same time numerous monitoring tasks and/or communications from the healthcare provider to the patient are automated saving the healthcare provider time and thereby increasing their efficiency.

A platform comprises one or more customized software applications (or "applications") configured to interact with one another. Applications of a platform as described herein are configured to provide monitoring and communication features.

In some embodiments of the platform, the platform includes one or more hardware components (e.g. one or more sensing devices).

In some embodiments, a platform is configured to operate together with one or more devices and/or one or more systems. That is, a device as described herein, in some embodiments, is configured to run an application of a platform using a built-in processor, and in some embodiments, a platform is utilized by a system comprising one or more computing devices that interact with or run one or more applications of the platform. A method as described herein includes, for example, steps for connecting a patient and a healthcare provider using a platform as described herein.

A platform comprises one or more applications, wherein at least one application comprises a patient application and one application comprises a healthcare provider application. In some embodiments, a platform comprises an additional monitoring application (i.e. in addition to the patient and healthcare provider application) that is located on a computing device at a remote monitoring location. For example, a third party, in some embodiments, has a monitoring application that allows the third party to monitor and/or interact with one or more applications of one or more platforms. For example, a monitoring service that monitors patient data would utilize a monitoring application.

FIG. 1 shows an exemplary embodiment of a platform as described herein comprising a digital processing device 101. The digital processing device 101 includes either a patient application or a physician application as described herein. The device 101 is configured to run the application. The digital processing device 101 includes a central processing unit (CPU, also "processor" and "computer processor" herein) 105, which is either a single core or multi-core processor, or a plurality of processors for parallel processing. The digital processing device 101 also includes either memory or a memory location 110 (e.g., random-access memory, read-only memory, flash memory), electronic storage unit 115 (e.g., hard disk), power source 125, and communication interface 120 (e.g., network adapter) for communicating with one or more other systems, and peripheral devices 135. The memory 110, storage unit 115, interface 120 and remote devices 135 are configured to communicate with the CPU 105 through a communication bus (solid lines), such as a motherboard. The digital processing device 101 is, in some embodiments, operatively coupled to a computer network ("network") 130 with the aid of the communication interface 120. The network 130, in some embodiments, comprises the Internet. The network 130 in some embodiments is a telecommunication and/or data network.

The CPU 105 is configured to execute machine-readable instructions embodied in a software application or module. The instructions may be stored in a memory location, such as the memory 110.

The storage unit 115 in some embodiments is configured to store files, such as user data, e.g., user preferences, and user programs.

Certain methods as described herein are implemented by way of machine (e.g., computer processor) executable code stored on an electronic storage location of the digital processing device 101, such as, for example, on the memory 110 or electronic storage unit 115. The machine executable or machine readable code is provided in the form of a software application or software module. During use, the code is executed by the processor 105. In some cases, the code is retrieved from the storage unit 115 and stored on the memory 110 for ready access by the processor 105. In some situations, the electronic storage unit 115 is precluded, and machine-executable instructions are stored on memory 110.

In some embodiments, a remote device 135 is configured to communicate with the digital processing device 101, and comprises any mobile computing device, non-limiting examples of which include a tablet computer, laptop computer, smartphone, or smartwatch. In some embodiments, a remote device 135 comprises a physiologic sensor.

The applications as described herein (i.e. patient application, healthcare provider application, and monitoring application) comprise one or more software modules. Software modules as described herein comprise computer readable and executable code. In various embodiments, a software module comprises a file, a section of code, a programming object, a programming structure, or combinations thereof. In further various embodiments, a software module comprises a plurality of files, a plurality of sections of code, a plurality of programming objects, a plurality of programming structures, or combinations thereof. In various embodiments, the one or more software modules comprise, by way of non-limiting examples, a web application, a mobile application, and a standalone application. In some embodiments, software modules are in one computer program or application. In other embodiments, software modules are in more than one computer program or application. In some embodiments, software modules are hosted on one machine. In other embodiments, software modules are hosted on more than one machine. In further embodiments, software modules are hosted on cloud computing platforms. In some embodiments, software modules are hosted on one or more machines in one location. In other embodiments, software modules are hosted on one or more machines in more than one location.

A computing device as described herein includes an operating system that enables it to run the software applications of the disclosure. Non-limiting examples of such operating systems are: Android, iOS, Chrome, Windows 10 Mobile, Blackberry 10, Firefox OS, Sailfish OS, Tizen, Ubuntu Touch OS, and H5OS. Non-limiting examples of manufacturers that produce said mobile computing devices compatible with the software applications disclosed herein are: Apple, Samsung, Sony, HTC, LG, and Motorola Mobility.

Sensing Device

In some embodiments of a platform, one or more sensors (or "sensing devices") are configured to monitor one or more physiologic parameters of an individual. In some embodiments, a local sensing device, for example, a sensing device located with a patient, is configured to communicate with one or more remote computing devices. As used here, a remote computing device is either a device not located with the patient or one that is not integrated with a computing device on which the patient application is running.

A sensing device, in some embodiments, is integrated with a patient computing device. For example, a sensing device comprising one or more ECG electrodes is integrated into a housing and/or processor of a computing device such as a smartphone or smartwatch. A sensing device, in some embodiments, operably couples to a patient computing device. For example, a sensing device having a coupler such as a magnetic or adhesive coupler is configured to couple with a computing device via the magnetic or adhesive coupler. In some embodiments, a sensing device is integrated with a housing of a protective case for a smartphone. In some embodiments, a sensing device is integrated with a watch band of a smartwatch.

A sensing device, in some embodiments, comprises a stand-alone device configured to transmit data to a patient application and/or a healthcare provider application. Non-limiting examples of sensing devices configured to operate with the platform described herein include thermometers, heart-rate sensors, activity sensors (e.g. an accelerometer, a gyroscope), location sensors (including position sensors), blood pressure sensors, oxygen saturation sensors, weight sensors (e.g. a scale), sweat sensors (e.g. a capacitive sensor), respiration sensors, EEG sensors, and ECG sensors.

Patient Application

A patient application is configured to be operated by a patient and a healthcare provider application is configured to be operated by a healthcare provider. In some embodiments of the platform, a patient application is on a computing device that is located with the patient and is remotely located from a healthcare provider.

A platform is configured so that one or more patient applications are linked to one or more health care provider applications. For example, data and communications are transmitted back and forth from patient to healthcare provider and from healthcare provider to patient through one or more applications of the platform. In certain embodiments, data received from a patient application results in a computer-generated response from an application within the platform (e.g. a healthcare provider application or a monitoring application).

A patient application is configured to monitor the health of a patient in either an episodic or continuous fashion. One manner in which the patient application continuously monitors the health of a patient is in an embodiment in which a sensor is continuously worn, contacted, or otherwise engaged by a patient.

A patient application is configured to receive, organize, and/or track patient data including sensed physiologic parameters. For example, a patient application is configured, in some embodiments, to receive a heart rate of a patient from a heart rate sensor. For further example, in some embodiments, a patient application is configured to receive a sensed ECG of a patient.

A patient application, in some embodiments, is configured to receive multiple health metrics or physiologic parameters. For example, the patient application comprises one or more interfaces presented to the patient that allow for the sensing and receiving of several parameters. Non-limiting examples of sensed patient parameters received by a patient application include an ECG, blood pressure, heart rate, height, weight, age, and physical activity level.

The patient application, in some embodiments, is configured to provide simultaneous measurement and sensing of cardiac health data. In addition, the patient application, in some embodiments, is configured to transmit data (e.g. cardiac health data or notifications) to another application within the platform. Transmission of sensed data to another application within the platform occurs simultaneously to the sensing of the data in some embodiments of the platform.

In some embodiments, the patient application is configured to organize and/or track data received from a sensing device, whereas in alternative embodiments a second, possibly remote, application organizes and tracks data received from a sensing device. Organizing received data on a patient application, in some embodiments, comprises sorting the data in a searchable patient interactive database. In some embodiments of the patient application, tracking received data comprises monitoring for specific data values or data ranges within the received data. In some embodiments, sensed data is transmitted directly to a healthcare provider application without being transmitted to a patient application.

A patient application is configured to work on or in conjunction with a computing device. For example, a first computing device comprises one or more sensors (either physically integrated with the computing device or not physically integrated with the computing device) configured to sense a physiologic parameter of a patient. For example, a patient may utilize an ECG monitor, a blood pressure monitor or a pulse oximeter, and the patient application to record and save or store his or her cardiac electric activity and blood pressure. Furthermore, the patient may elect to send said cardiac electric activity and blood pressure data or oxygen saturation data to his or her healthcare provider via the software application of the disclosure. Furthermore, the patient application, in some embodiments, is configured to simultaneously monitor and/or record multiple physiologic parameters.

Sensed data is transmitted to an application of the platform (e.g. patient application, healthcare provider application, monitoring application) either through a wired connection wireless connection via, for example, a WiFi transmitter, a Bluetooth transmitter, an audio or ultrasound acoustic transmitter.

A patient application comprises one or more interfaces (e.g. a graphical interface, an audio interface, a video interface). One or more patient interfaces of the software applications enable the patient to: for example, obtain physiological information from a sensing device or from other health-based software applications (e.g. Apple Health), store sensed data from a sensing device, transmit and receive communications, track completion of tasks, and/or transmit physiological, audio, and visual data to a healthcare provider.

In some embodiments of the patient application, the patient application is configured to communicate with another application running within the platform described herein, and, in some embodiments, is also configured to communicate with software applications that are not a part of the platform in order to transfer and/or receive data such as height, weight, age, physical activity level, heart rate, blood pressure, and/or ECG data from a sensing device. For example, in some embodiments, the patient transfers to and/or receives data from other health based software applications including, but not limited to, Apple Health, Google Fit, S Health, and/or Fitbit and save it to his or her cardiac monitoring device.

The patient application provides patients with one or more patient interfaces that provide for selection by the patient of specific data to be transmitted to a healthcare provider, and/or data that may be transmitted from the patient application to the healthcare provider automatically. Data transmitted to a healthcare provider application from the patient application comprises, for example, height data, weight data, age data, physical activity level data, heart rate data, blood pressure data, and ECG data.

Figure 2A:
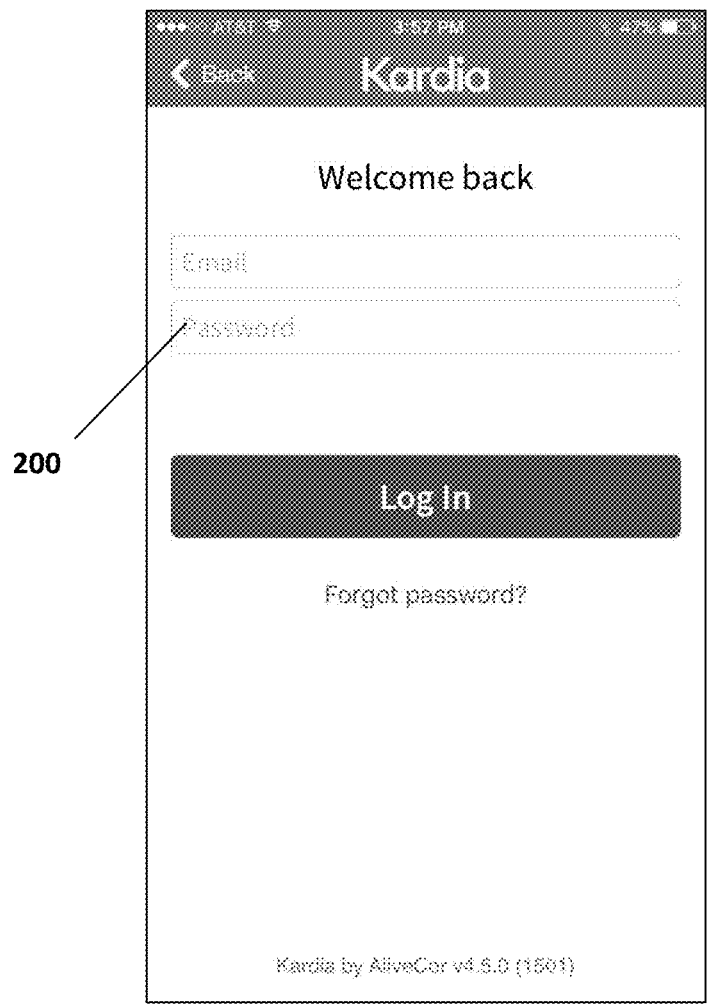
FIG. 2A shows an embodiment of an initial home screen interface a patient encounters when he or she has not yet signed into a patient application that is operating on a computing device as described herein.

FIG. 2A shows an embodiment of an initial home screen interface encountered by a patient when he or she has not yet signed into a patient application that is operating on a computing device as described herein. The patient application typically includes a log in feature 200 that prompts the patient to provide, for example, his or her email and password in order to log in.

In some embodiments, either the entire patient application or a portion of the application is provided to the patient in a locked state, where in order to operate the application or a portion of the application, a patient must first be granted access by another party (e.g. a healthcare provider, hospital, employer, or insurance provider). For example, a healthcare provider grants a patient access to the patient application by providing the patient with a traditional prescription or an e-prescription containing an access code or password through which a patient obtains access to the locked patient application or locked portion of the patient application by entering the password as a login and/or password in the login-in feature 200. In some embodiments of the applications described herein, an e-prescription comprises an email sent from the healthcare provider to the patient (or caused to be sent by the healthcare provider application to the patient) that contains an access code or password to access the software application. In another example, a healthcare provider provides an e-prescription comprising a hyperlink that when clicked on by the patient unlocks the patient application or a locked portion thereof. In another example, a healthcare provider sends a patient a text message containing either a link or a code that is used by the patient to unlock the patient application or a portion thereof. In some embodiments of the platform, access to the patient application is automatically granted by the platform in response to a request by a healthcare provider.

In another example, a healthcare provider provides a patient with an e-prescription for a health monitoring device that utilizes and/or includes a patient application as described herein. For example, a healthcare provider provides a patient with a prescription for a device that is configured to run the patient application as described herein. For further example, a cardiologist provides the patient with an e-prescription for a device comprising electrodes that is configured to sense an ECG of the patient and interface with the patient application which was also prescribed to the patient.

Once a patient accesses the patient application by entering an access code or password provided by another party (e.g. a healthcare provider, hospital, employer, or insurance provider), the patient application, in some embodiments, displays an image associated with the healthcare provider such as, for example, an image of a healthcare provider and/or one or more logos associated with the healthcare provider and/or the healthcare provider's practice and/or a hospital associated with the healthcare provider.

Figure 2B:
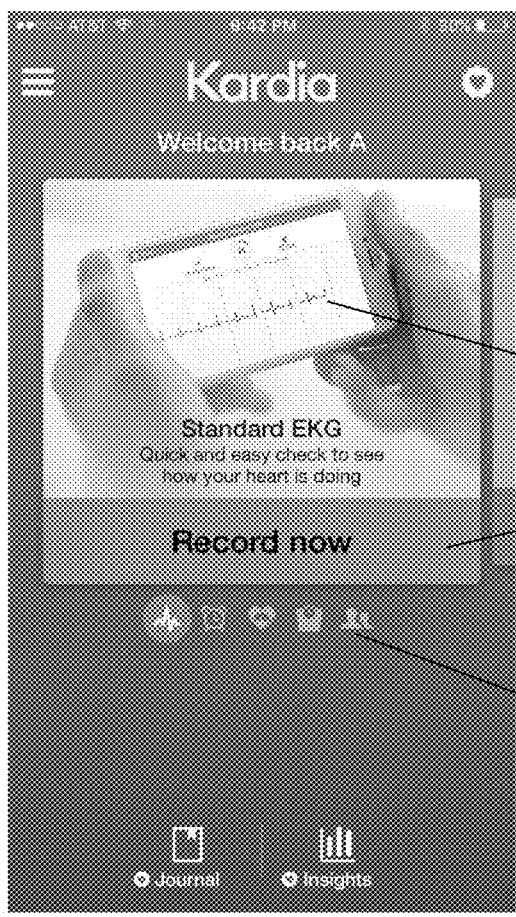
FIGS. 2B-E show screenshots of exemplary interfaces of a patient application that are viewed by the patient once the patient logs in to the patient application.
Figure 2C:
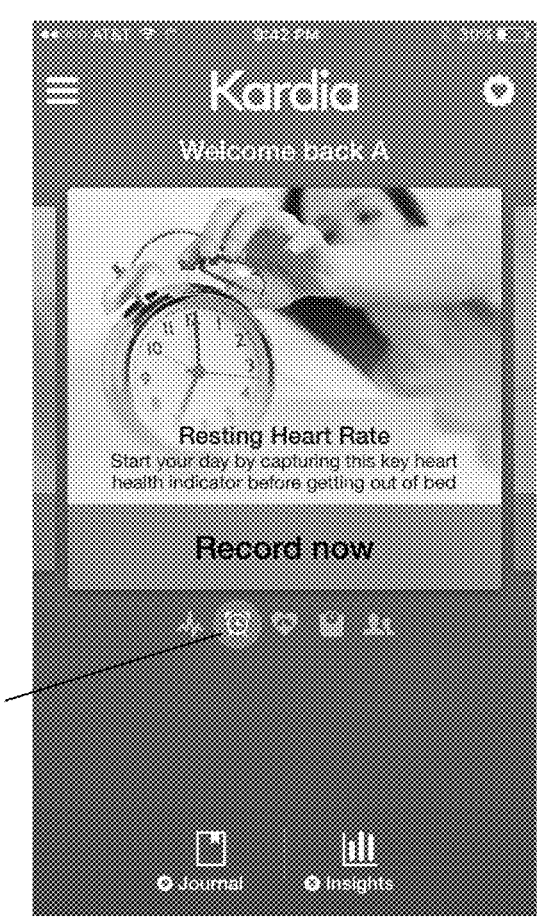
Figure 2D:
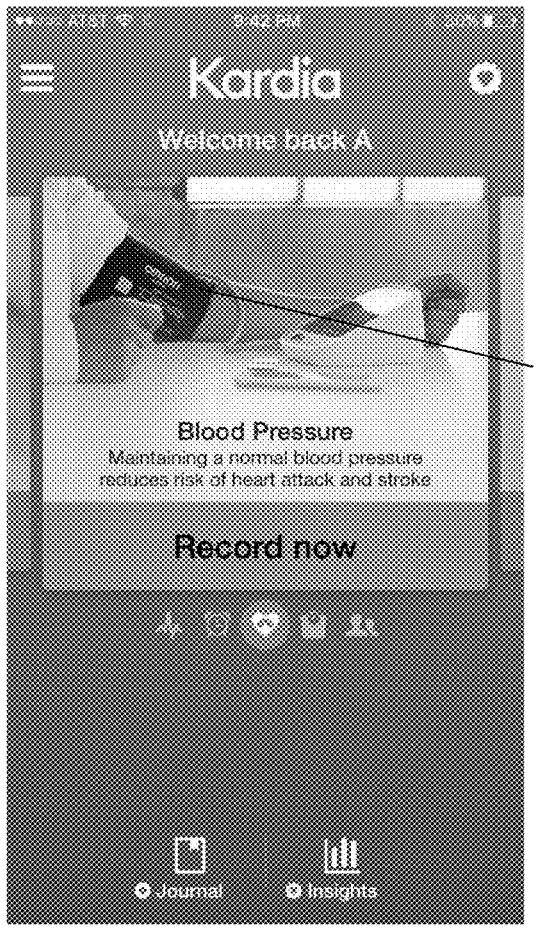

FIGS. 2B-E show screenshots of exemplary interfaces of a patient application that are viewed by the patient once the patient logs in to the patient application. FIGS. 2B and 2C show a patient interface component 204 that provides the patient with the ability to select to record an ECG or a heart using, for example, an ECG sensing device 200 that is configured to interact with the software application. The patient interface component 204, in some embodiments, comprises a touchscreen button.

Figure 2E:
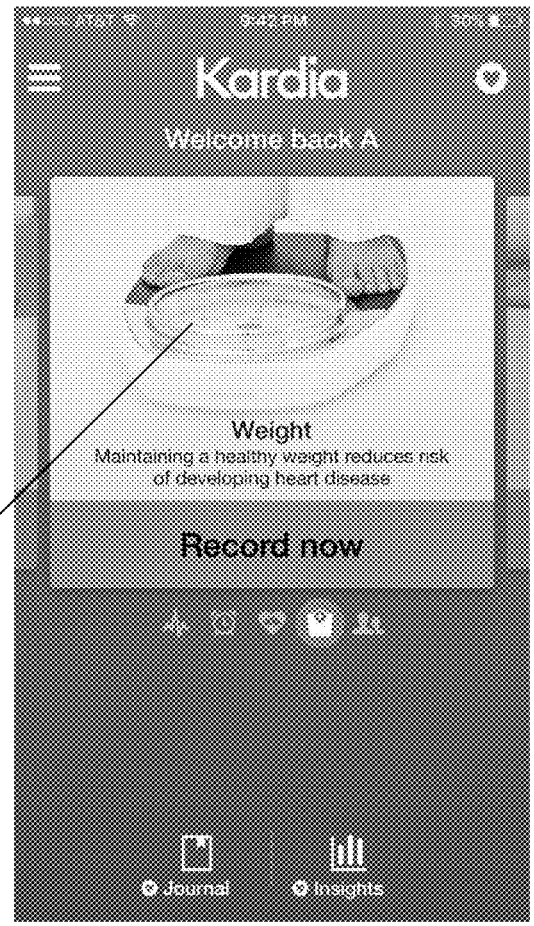

In some embodiments of the patient application, a patient interface comprises a dashboard 210 and/or interface 204, which the patient engages with in order to carry out a task such as sense, for example, one or more physiologic parameters using a sensing device such as, for example, resting heart rate (FIG. 2C), blood pressure (FIG. 2D), physical activity, and weight BMI (FIG. 2E). In some embodiments, when engaged by the patient, interface 204 causes the sensing of a physiologic parameter of a patient by a sensing device 200, 206, or 208 (which are depicted on the screen shot of the patient application in the exemplary embodiments of FIGS. 2B-E). First sensing device 200 comprises a smartphone operably coupled to one or more ECG electrodes (not shown). As described herein, in some embodiments, a patient application is running on the first sensing device 200. A second sensing device 206 comprises a blood pressure cuff and a third sensing device 208 comprises a scale. As described herein, in some embodiments, a patient application receives sensed data transmitted from a sensing device on which it is not running such as, for example, embodiments of the second and third sensing devices 206 and 208.

Figure 3:
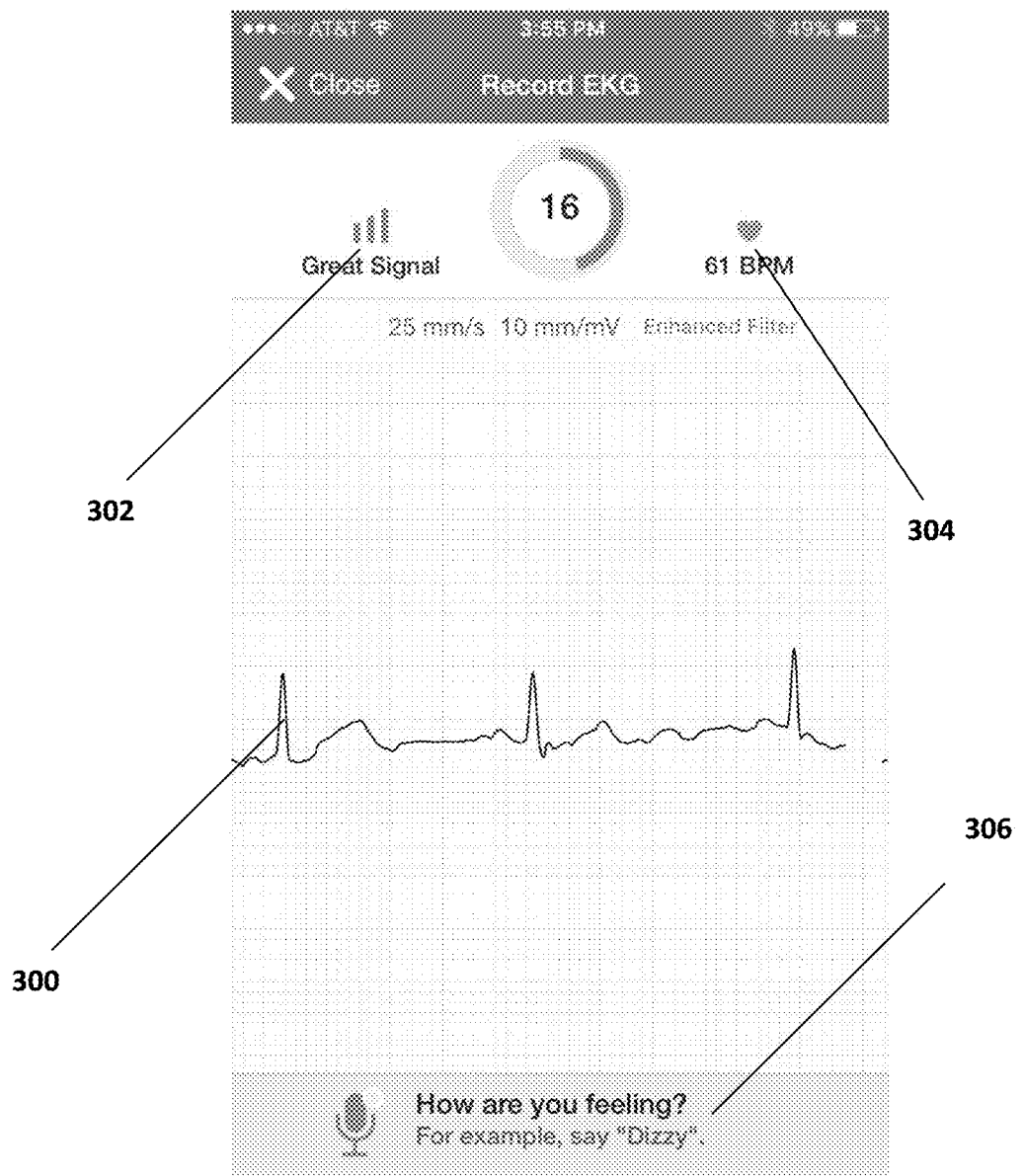
FIG. 3 shows a screenshot of an exemplary patient interface a patient encounters during the sensing of an ECG.

FIG. 3 shows a screenshot of an exemplary patient interface a patient encounters during the sensing of an ECG—displayed on the interface at 300—using an ECG sensing device. In some embodiments of the patient application, a patient is able to select an option in the patient interface, for example, using a touchscreen button 306 that allows the patient to record audio and/or video using a computing device that is interacting with the patient application (e.g. a smartphone that is running the patient application as an app). For example, a patient may sense an ECG with an ECG sensing device, transmit the sensed ECG to a processor on a computing device (e.g. a smartphone or a smartwatch), and record an audio and/or video recording that the patient application associates with the sensed ECG. For example, a patient may record an audio recording that says "I'm having chest pain" together with a sensed ECG. The patient application is configured to associate the sensed ECG together with the recorded audio and/or video recording and store them locally on a computing device interacting with the patient application and/or transmit ECG and audio and/or video recording together to another computing device (e.g. a computing device of a healthcare provider or monitoring service). The patient interface component may prompt the patient to verbally state any notes the patient has to add by, for example, engaging the patient interface at 306 by touching the touch-screen interface at 306. Once engaged at 306, for example, the patient verbally describes any symptoms he or she is experiencing, for example, during that day or while the ECG is being sensed. Such verbal (e.g. video or audio) description is recorded by the patient application and transmitted to a physician application and/or a monitoring application and/or stored. The addition of verbal notes by the patient to the ECG data provides for a correlation between symptoms and cardiac health metrics. Heart rate displayed on the exemplary interface at 304 and other parameters specific to ECG data such as filter, gain, and speed are displayed on the ECG measurement interface at 302 in some embodiments or are provided as metadata.

A patient application, in some embodiments, displays sensed patient data via a patient interface such as the exemplary interface displayed in FIG. 3. One or more health metrics displayed in the patient interface are displayed graphically or textually. The patient interface may also display an ECG at 300 and heart rate recordings at 304 over a period of time; the ECG, heart rate recordings, and time may be displayed graphically or textually.

The patient interface may further, for example, display the status of an ECG measurement, wherein the status may reflect: a normal ECG measurement and may be labeled as "normal;" or an abnormal ECG measurement may be labeled as "atrial fibrillation." In other aspects, the patient dashboard interface may enable the patient to add notes to each recorded health metric In some embodiments of the patient application, the data in the patient interface of the patient application is also viewable by the healthcare provider application. That is, in a platform wherein a healthcare provider and a patient are running software applications on their respective computing devices, a healthcare provider, in some embodiments of the platform, is able to view the patient's patient interface as it appears to the patient using the healthcare provider application running on a computing device of the healthcare provider. Alternatively, the data may be viewed in the healthcare provider application at time later than acquisition of the data.

Figure 4A:
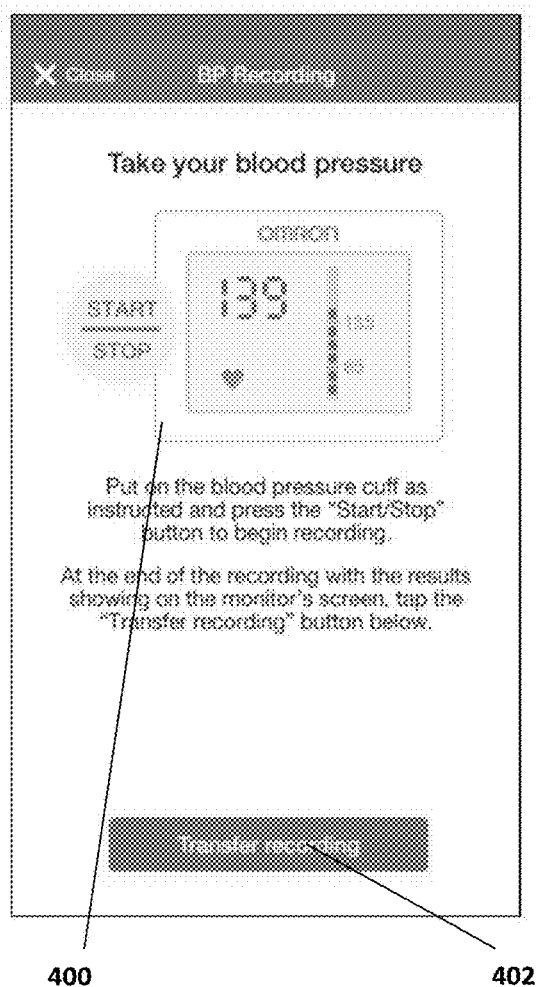
FIG. 4A shows a screenshot of an exemplary patient interface during sensing of a physiologic parameter comprising a blood pressure measurement.

FIG. 4A shows a screenshot of an exemplary patient interface during sensing of a physiologic parameter comprising a blood pressure measurement. A sensing device, in some embodiments, comprises a blood pressure monitor comprising an electronic sphygmomanometer configured to sense a patient blood pressure and transmit the sensed blood pressure to the patient application. In some embodiments. a patient is prompted to record a blood pressure measurement by the patient application through the transmission of an alert or alarm 400 displayed on the interface or otherwise transmitted through a computing device interfacing with the patient application. The patient is then prompted, in some embodiments, to transfer the blood pressure recording from the blood pressure device to the patient application by, for example, engaging touchscreen button 402, and furthermore, the patient may store said blood pressure recording in a computing device via the patient application, whereas, in some embodiments, storage and transmission of a sensed parameter is done automatically.

Figure 4B:
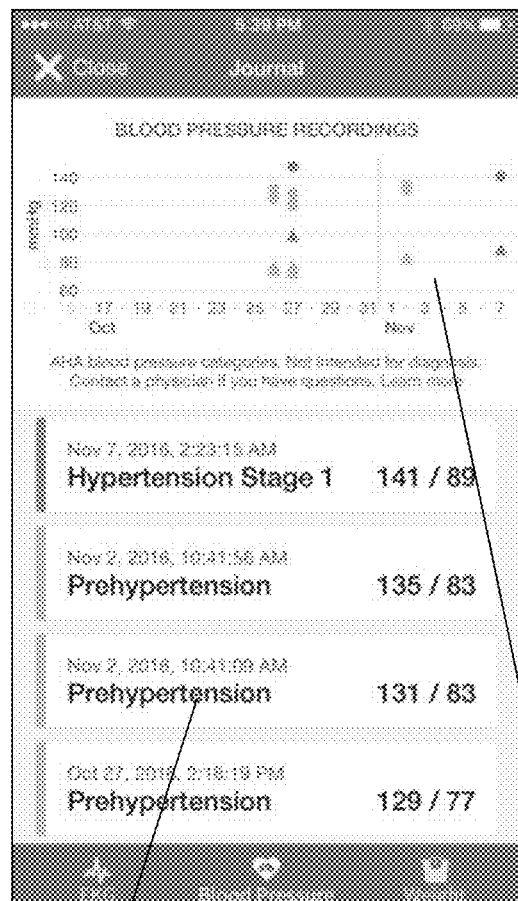
FIG. 4B shows an exemplary screenshot of a patient interface showing recorded blood pressure measurements over a period of time.

As shown in FIG. 4B, which shows an exemplary screenshot of a patient interface, a patient is able to view stored blood pressure recordings over a period of time as depicted graphically at 404. The patient interface shown in FIG. 4B further displays at 402 the most recent recordings to the patients by labeling them as "new" and including the time on which the blood pressure recording was saved. In addition, the patient may view other metrics sensed over a period of time such as, for example, stored weight and BMI recordings over a period of time.

Figure 5:
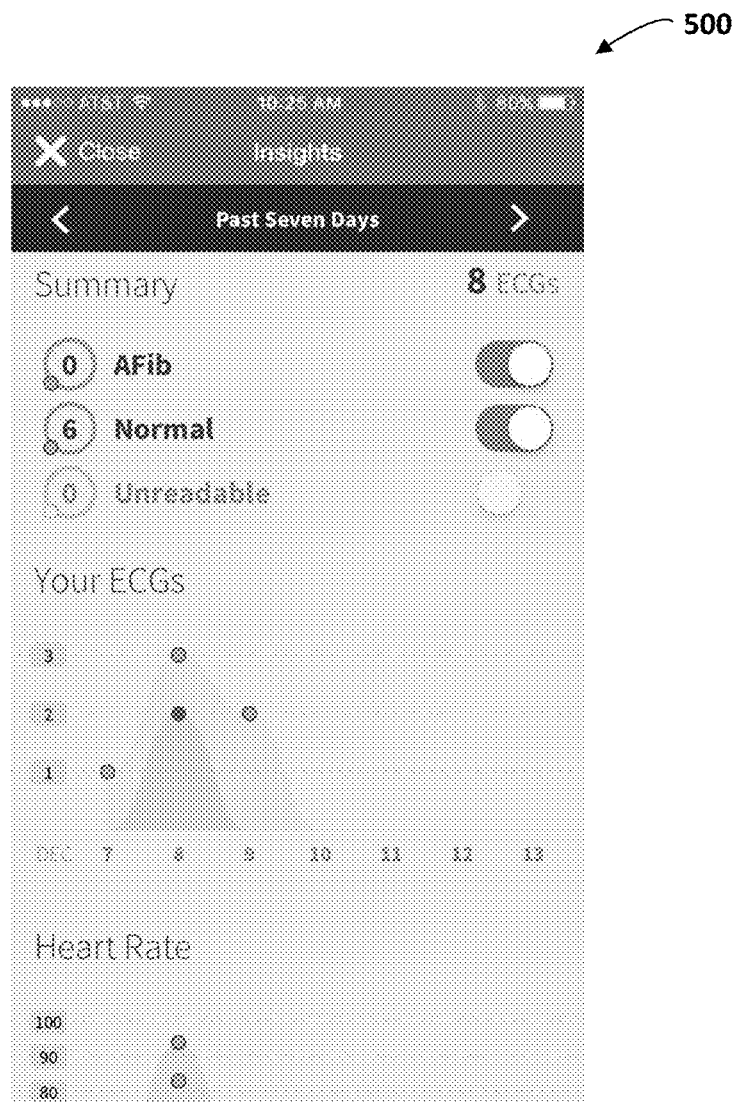
FIG. 5 shows an exemplary screenshot of a patient interface 500 displaying multiple historical physiologic measurements and includes analysis and/or insights regarding the physiologic parameters.

FIG. 5 shows an exemplary screenshot of a patient interface 500 displaying multiple historical physiologic measurements and includes analysis and/or insights regarding the physiologic parameters. For example, interface 500 is configured in some embodiments to display graphical representation of one or more physiologic parameters sensed over time. For example, interface 500 is configured in some embodiments to display an assessment of a sensed physiologic parameter such as if the sensed parameter is normal or abnormal.

Figure 6:
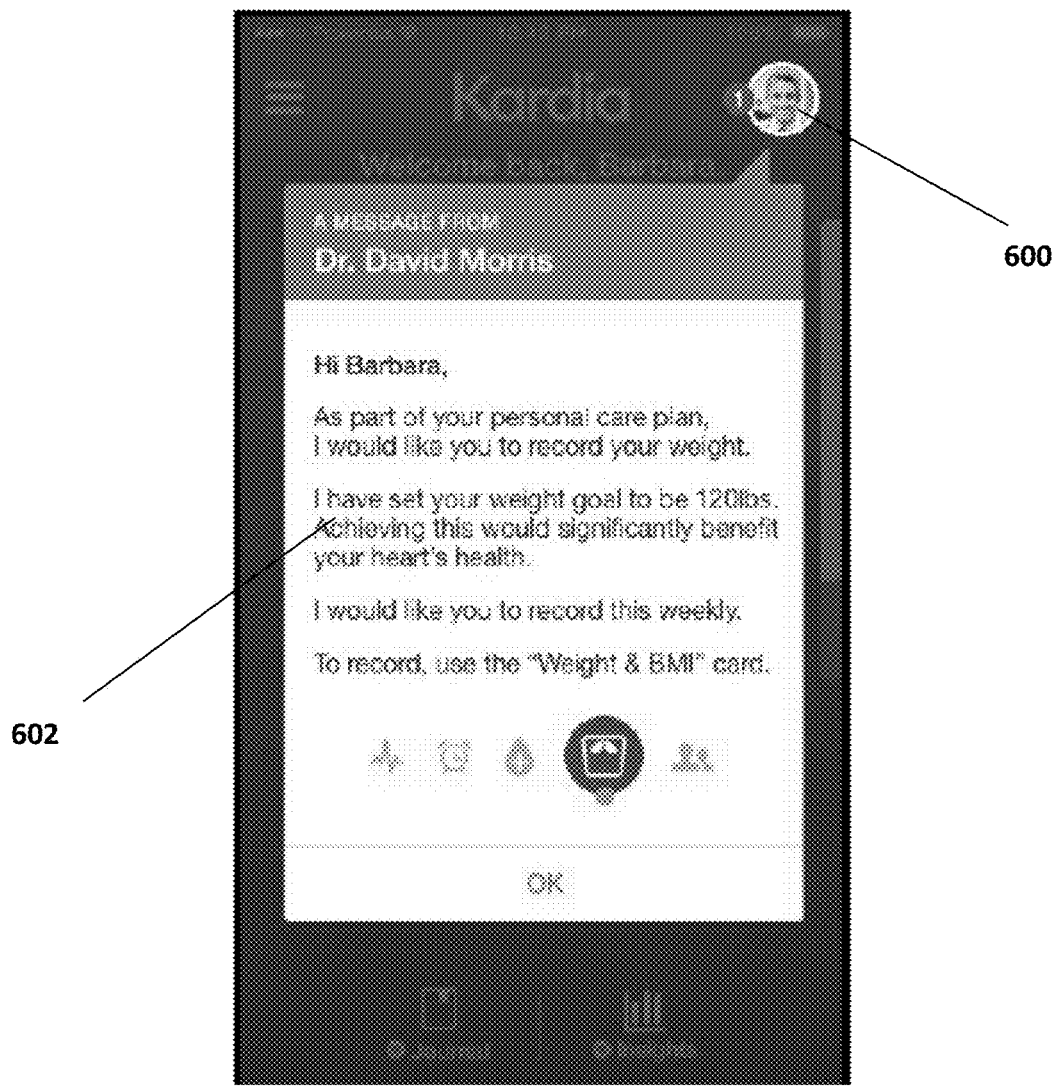
FIG. 6 shows an exemplary screenshot of a patient application showing an exemplary healthcare provider communication.

FIG. 6 shows an exemplary screenshot of a patient application showing an exemplary healthcare provider communication 602. A communication to a patient through the platform is either sent directly from a healthcare provider or is automatically generated and contains an indicia 600 that it was generated by a healthcare provider (i.e. even though it was generated automatically).

An automatically generated communication as described herein is a computer generated communication yet it has indicia of having been created and transmitted by a healthcare provider. In this way, a patient is given the impression that a computer generated communication was created and generated by a healthcare provider. An example of a computer generated communications includes a communication of congratulation to a patient for successfully completing a task such as, for example, losing 5 pounds of weight. In some embodiments of the platform described herein, a computer generated communication contains indicia that the communication was generated and transmitted by a healthcare provider such as, for example, an electronic message containing an image of the healthcare provider or a logo associated with the healthcare provider. It is very beneficial to automatically generate (i.e. computer generate) such communications rather than having a healthcare provider generate them in that it saves the healthcare provider time in monitoring and responding to routine patient monitoring changes. While at the same time the indicia of the communication having originated from the healthcare provider provides emotional benefits to the patient. Computer generated communications are one way in which the platform as described herein functions as a healthcare provider extender or assistant, saving the healthcare provider time while providing valuable patient monitoring and feedback.

The applications of the present disclosure also provide patients with a patient interface where the tasks provided by a healthcare provider are received and displayed. In this case, as shown in FIG. 6, a healthcare provider has provided to the patient a care plan comprising of recording his or her weight.

The software application also provides an interface where push notifications sent by the healthcare provider are received and displayed. An additional interface component, in some embodiments, allows the patient to track or affirm completion of various health-related tasks such as physical activity or taking medications.

Figure 7:
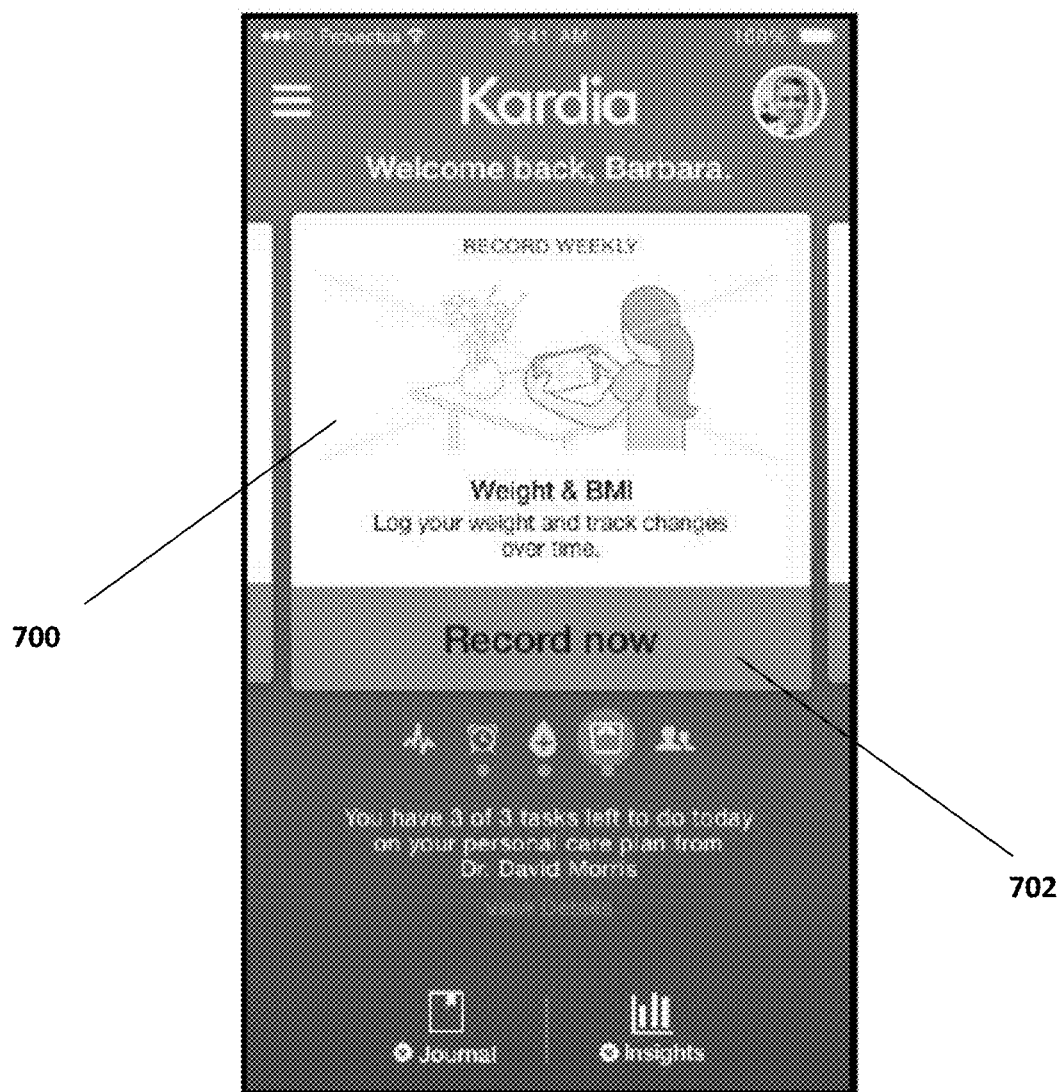
FIG. 7 shows a screenshot of an exemplary patient interface on a patient application, wherein a patient is given a task that corresponds to a patient care plan.

FIG. 7 shows a screenshot of an exemplary patient interface on a patient application, wherein a patient is given a task 700 that corresponds to a patient care plan (in this case, the care plan of FIG. 6). Once the patient engages with a scale, in some embodiments, pressing a touchscreen button 702 causes the transmission of data from the scale (while in others, the scale does so automatically), or alternatively the patient inputs the weight data into the interface and affirms the data by selecting a button.

In some embodiments, a healthcare provider application is configured to generate a comprehensive patient care plan using received patient data. The patient care plan, for example, is transmitted to a patient application and, for example, is configured to monitor, record, and/or track multiple health metrics in a patient such as ECG, blood pressure, weight, physical activity levels, BMI, and medication compliance.

The healthcare provider applications described herein, in some embodiments, are configured to provide a patient with the ability to perform an exercise stress test in order to test for the presence heart disease. For example, a patient application instructs a patient to perform an exercise for a set period of time, such as walking on a treadmill for 20 minutes, while contacting an ECG sensing device that is in communication with the patient application, which, for some embodiments, transmits that data to the healthcare provider application for analysis.

An exercise stress test is used to aid in the diagnosis of cardiovascular disease. Specifically, the exercise stress test is performed by a healthcare provider in a professional clinic or medical center to determine the amount of stress that a patient's heart is able to withstand before developing either evidence of ischemia or an abnormal heart rhythm. Different types of stress tests may comprise a treadmill or exercise stress test, dobutamine or adenosine stress test, stress echocardiogram, or nuclear stress test. An exercise stress test is used to measure the effect of exercise on the heart. An exercise test performed in a professional clinic comprises monitoring a patient's cardiac electric activity as the patient walks on a treadmill. The healthcare provider monitors the patient's cardiac electric activity by placing electrodes in ten small areas of the patient's body, which are connected to an ECG monitor. The healthcare provider takes baseline measurements of blood pressure, ECG, and heart rate prior to commencing the exercise stress test. The exercise stress test begins when the patient starts walking on the treadmill for specific period of time. If any abnormal changes in the ECG or any chest pains develop, the test is stopped and such abnormal changes are noted.

In some embodiments, the patient application described herein may provide the patient with the ability to perform an at-home exercise stress test to test for heart disease. The patient may use the cardiac health monitoring device and the patient application to monitor cardiac electric activity, blood pressure, and heart rate while performing the exercise stress test. The patient application may instruct the patient to place a cardiac health monitoring device in contact with his or her skin, and take a baseline ECG measurement. The interface may further instruct the patient to take a baseline blood pressure measurement prior to starting the exercise stress test. The patient application may have an interface that prompts the patient to begin an exercise stress test. The interface may prompt the patient to walk for a determined amount of time while physically contacting the cardiac health monitoring device. For example, the patient may be using a smartphone or other mobile computing device, which incorporates sensing electrodes, as a cardiac health monitoring device to perform the at-home exercise stress test. Furthermore, the patient may use said smartphone (or other mobile computing device) comprising sensing electrodes and may place his or her hands over said sensing electrodes while he or she engages in walking as part of the exercise stress test. At the conclusion of the period of time, the heart rate is measured over 2 minutes to calculate the time required for the heart to recover from the exercise. The interface may comprise a component to provide the patient with the option to record, save, and/or send all data collected during the exercise stress test, once the stress test has been completed, which data may then be transmitted or shared with the healthcare professional in the healthcare professional application via transmitting means known to the skilled artisan.

Figure 8:
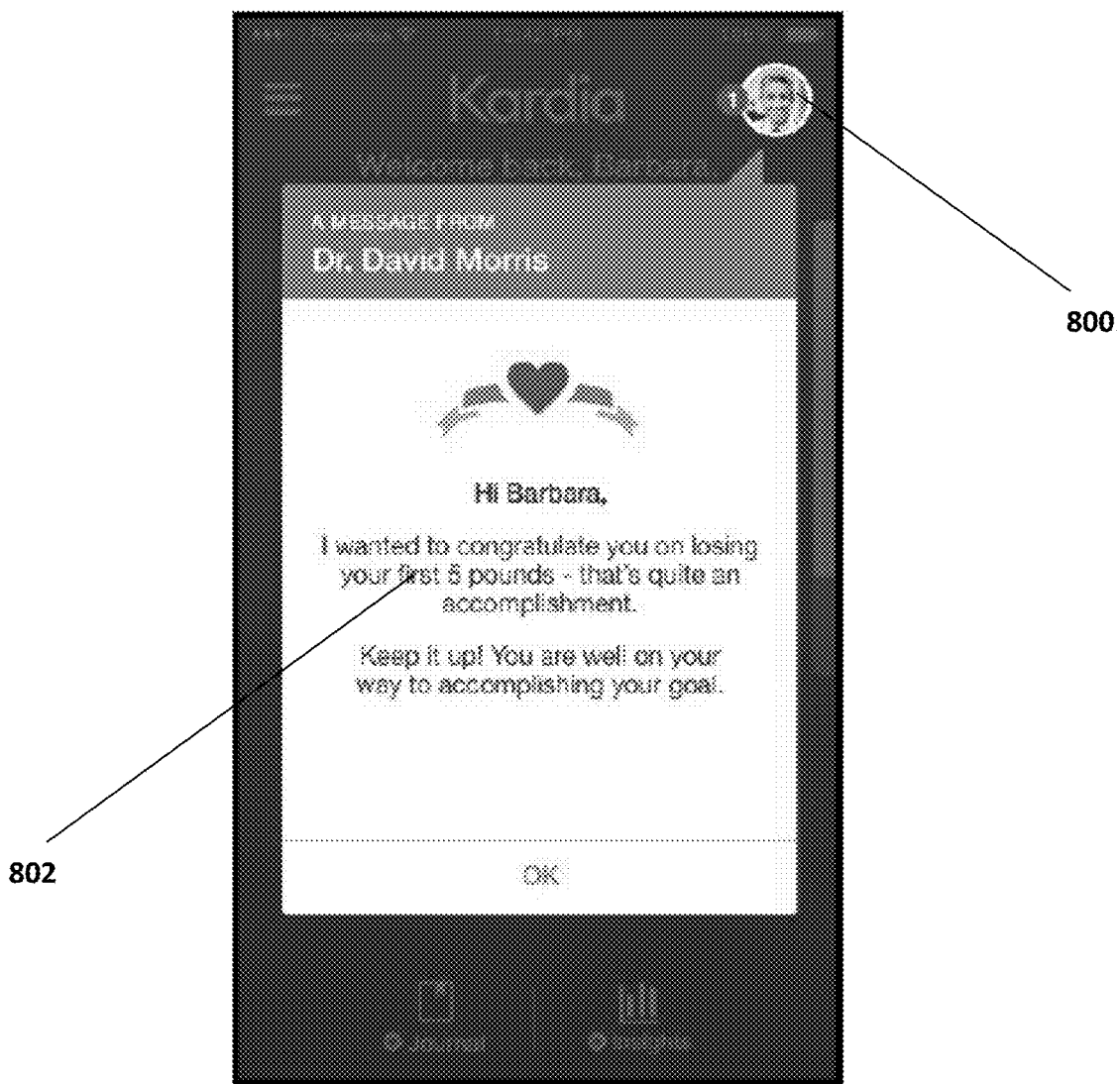
FIG. 8 shows a screenshot of an exemplary healthcare provider communication transmitted in response to received patient data.

FIG. 8 shows a screenshot of an exemplary healthcare provider communication transmitted in response to received patient data. In this case, the patient having successfully completed the care plan of FIG. 6 by recording and transmitting his or her weight as shown in FIG. 7 receives a congratulatory message. As described, such a healthcare provider communication is either generated and sent by the healthcare provider or is generated and sent automatically, for example, by the healthcare provider application.

As shown, an indicia 800 authenticates the healthcare provider generated and transmitted the message and may include an image or logo of the healthcare provider. A healthcare provider communication 802 is generated automatically, in some embodiments, when a patient achieves a certain goal as indicated by received sensed physiologic data. In this example, once a patient achieves a goal weight, a congratulatory communication 802 is automatically sent to the patient application. In some embodiments, a patient communication references achievement of a goal or task, such as, for example, a patient sending an email to the healthcare provider application that states that the patient achieved a weight loss goal. In some embodiments, a patient communication referencing a specific physiologic parameter or achievement of a task (e.g. weight loss) is analyzed by an algorithm that in response generates an automatic healthcare provider communication.

As shown, in some embodiments, a healthcare provider communication references the received sensed data that triggered the sending of the healthcare provider communication. For example, a patient instructed to lose ten pounds and transmits data or a communication indicating that he or she has successfully done so receives a congratulatory message referencing the ten pound weight loss or weight loss generally.

In general, behavioral notifications may be sent by the healthcare provider to a patient of their choice. The behavioral notifications sent to patients by healthcare providers may be automatically generated. The notifications sent to patients may be personalized push notifications that are automatically generated and sent to patients when patients complete a prescribed task. For example, a healthcare provider's application may automatically generate and send a push notification to a patient congratulating a patient for achieving a prescribed task. Examples of prescribed tasks may be performing a physical activity, losing weight, decreasing BMI points, recording ECG data, and/or recording blood pressure measurements.

Behavioral notifications may also be sent by a patient's family members. The software application of the disclosure may prompt the patient to "add" patients and connect with them via the software application. The family members that accept and connect with the patients may receive notifications when the patient achieves specific tasks such as correctly adhering to their prescription regimen. The family members may send a behavioral notification congratulating the patient for achieving their prescribed task.

Healthcare Provider Application

Figure 9A:
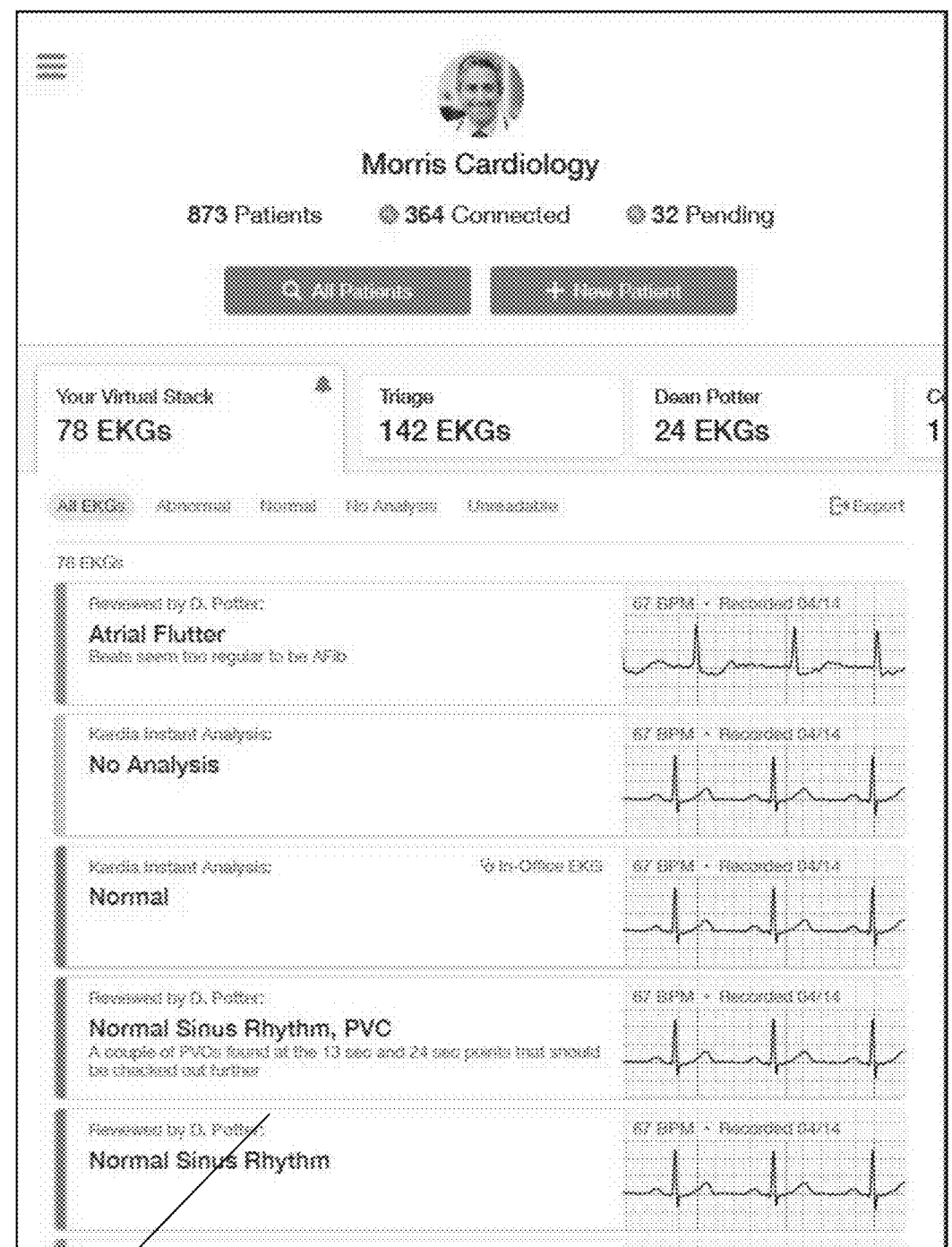
FIG. 9A shows a screenshot of an exemplary initial home screen interface of a healthcare provider application as would be viewed by a healthcare provider when browsing his or her list of patients using the healthcare provider application.

FIG. 9A shows a screenshot of an exemplary initial home screen interface of a healthcare provider application as would be viewed by a healthcare provider when browsing his or her list of patients using the healthcare provider application. In some embodiments of the healthcare provider application, the healthcare provider sorts his or her list of patients by other healthcare providers' names or technician's' name. In some embodiments of the software application, the initial home screen interface comprises a "virtual stack" 900 displaying, for example, all ECGs provided to the healthcare provider. For example, the interface may provide the healthcare provider with the option to select an ECG from a virtual stack of ECGs and view a 3 second segment of the ECG recording. The 3 second segment is displayed next to the reviewer and diagnostic information on the virtual stack 900. In some embodiments of the healthcare provider application, the 3 second segment is selected to be the ECG segment that is most representative of the diagnosis. The display of the entire ECG is used to quickly identify an ECG recording from a list in the different subfolders of the virtual stack (e.g. "All ECGs," "Abnormal," "Normal," "No Analysis," or "Unreadable").

A feature of the healthcare provider application, in some embodiments, is to receive and display patient data, as shown in FIG. 9A. Non-limiting examples of such patient data are height, weight, body mass index (BMI), age, physical activity level, heart rate, blood pressure, and/or ECG data. Patient data received by the healthcare provider is stored via the healthcare provider application in a computing device running or connected to the healthcare provider application. Furthermore, the healthcare application aids the healthcare provider in analyzing the data. For instance, the healthcare provider application, in some embodiments, comprises audio or video data analysis capabilities.

Figure 9B:
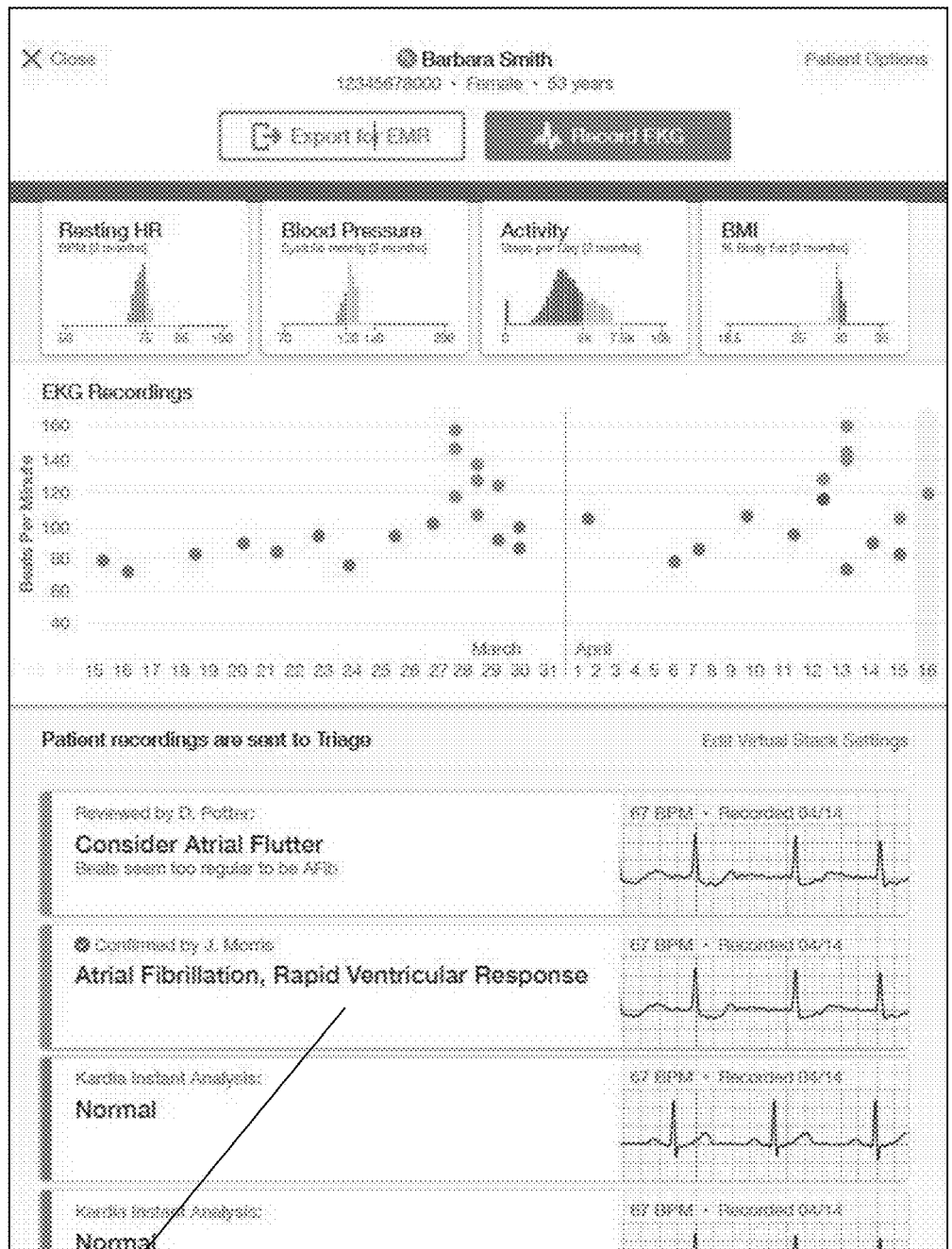
FIG. 9B shows a screenshot of an exemplary interface of a healthcare provider application displaying received data.

A healthcare provider application is configured to receive, organize, and/or track patient data received from one or more patient applications (e.g. from one patient or a plurality of patients). As shown in FIG. 9B at 902, a healthcare provider application is configured, to analyze and organize received ECG data (i.e. indicate if analysis reveals a possible abnormality).

The healthcare provider application is configured to analyze received patient data. For example, in some embodiments, a healthcare provider application is configured to calculate and generate risk scores based on patient population data. For example, a risk score may be calculated to predict the likelihood of an individual to suffer from cardiovascular disease in the future. Such algorithms, for example, use physiological data, such as ECG data, to recognize a patient's identity based on patient population data or to recognize a change in patient's health based on historical data for the patient. The software application may comprise machine learning algorithms, which improve analysis of an individual's data based inputting that data into a machine learning algorithm trained to predict health outcome probabilities for any number of health conditions. In addition, such algorithms may provide with unique identification of individual patients based on analysis of aggregate data such as ECG recordings or measurements. Unique identification of patients by machine learning algorithms may comprise identification of gender, identification of individual, identification of change in health, and/or identification of heart age. In some embodiments of the software application, heart age may be a representative age of a patient's heart that reflects the overall health of the patient's heart and a general indication of the patient's cardiac health. Similar to heart age, machine learning algorithms may also serve as a risk assessment tool to calculate a risk score used to predict the likelihood of an individual to suffer from cardiovascular disease in the future or to give the patient an overall perspective of their current cardiac health status. Machine learning algorithms may be used to predict a risk score and/or predict a change in health, whether negative or positive.

The healthcare provider's inbox interface may contain different folders, such as, but not limited to: a "triage" folder, a "healthcare provider's" folder, a "confirmed and archived" folder. The healthcare provider may move and organize data, such as patient's data, in said folders.

The healthcare provider application may alert the healthcare provider if certain data are received. For example, an interface of the healthcare provider's software application may show a list of notifications displaying information such as the patient's name, gender, age, phone number, and corresponding status update. In some embodiments of the software application, a status update may comprise a notification regarding a patient's ECG recording or the percentage of abnormal ECG data of a patient. Other examples of patient status updates that the healthcare provider may choose to activate notifications for are: possible atrial fibrillation detected, possible atrial fibrillation detected with heart rate surpassing a customizable number, heart rate surpassing a customizable number, heart rate under a customizable number, and no ECG data received in a customizable number of days. The frequency in which notifications are sent may be set to different parameters such as never, once, or always.

Figure 9C:
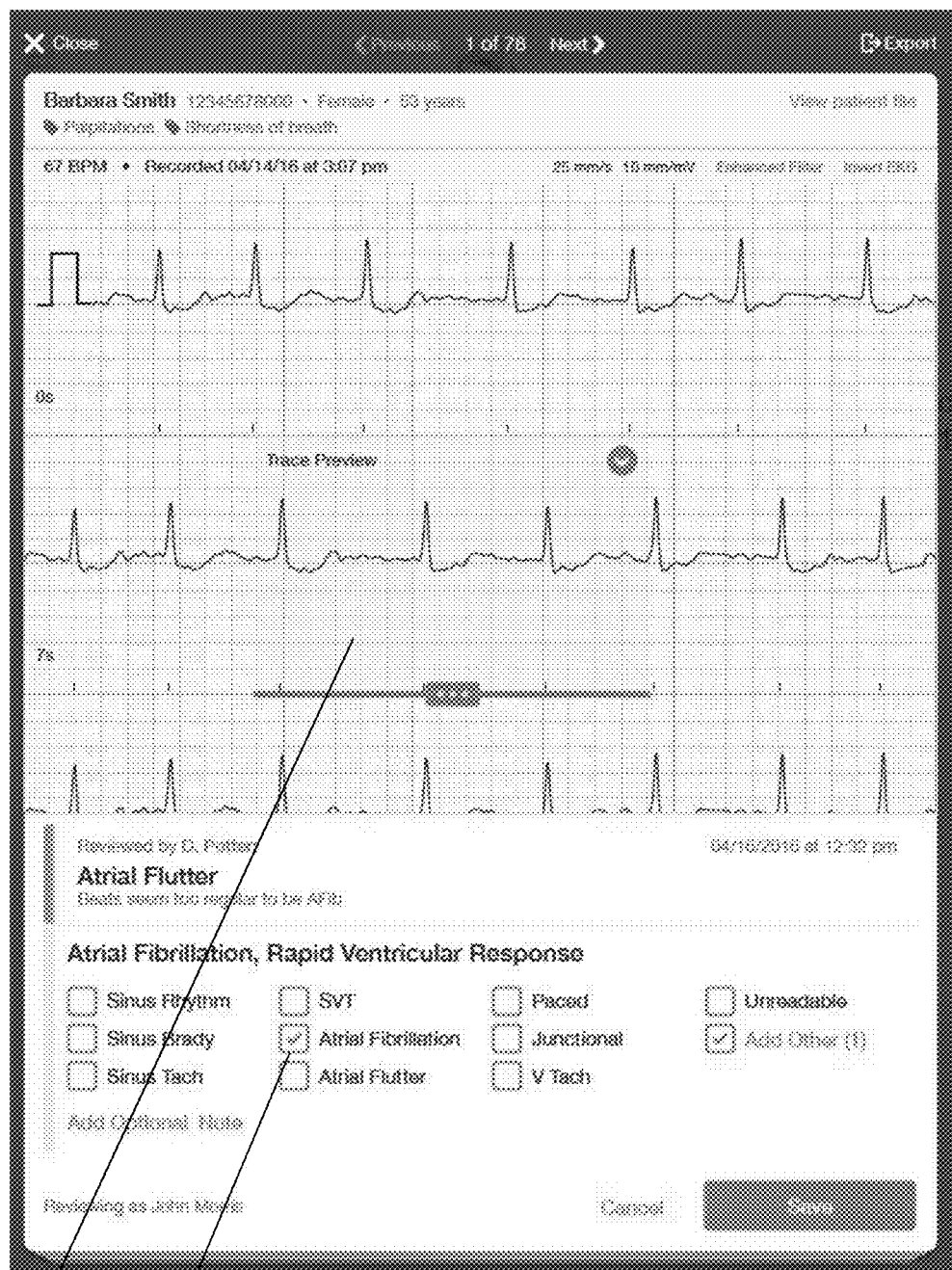
FIG. 9C shows a screenshot of an exemplary interface of a healthcare provider application that allows a healthcare provider to select a descriptor of a received patient ECG.

In some embodiments of the software applications described herein, the healthcare provider may add an interpretation to each ECG recording from the available options, which include: Sinus Rhythm, Sinus Brady, Sinus Tach, SVT, Atrial Fibrillation, Atrial Flutter, Paced, Junctional, V Tach, or Unreadable, as shown in FIG. 9C. As shown, in some embodiments, a highlighting tool 904 allows a healthcare provider to select a particular ECG segment, and an interactive check-box formatted list 906 allows a healthcare provider to choose an assessment of the highlighted ECG.

Figure 9D:
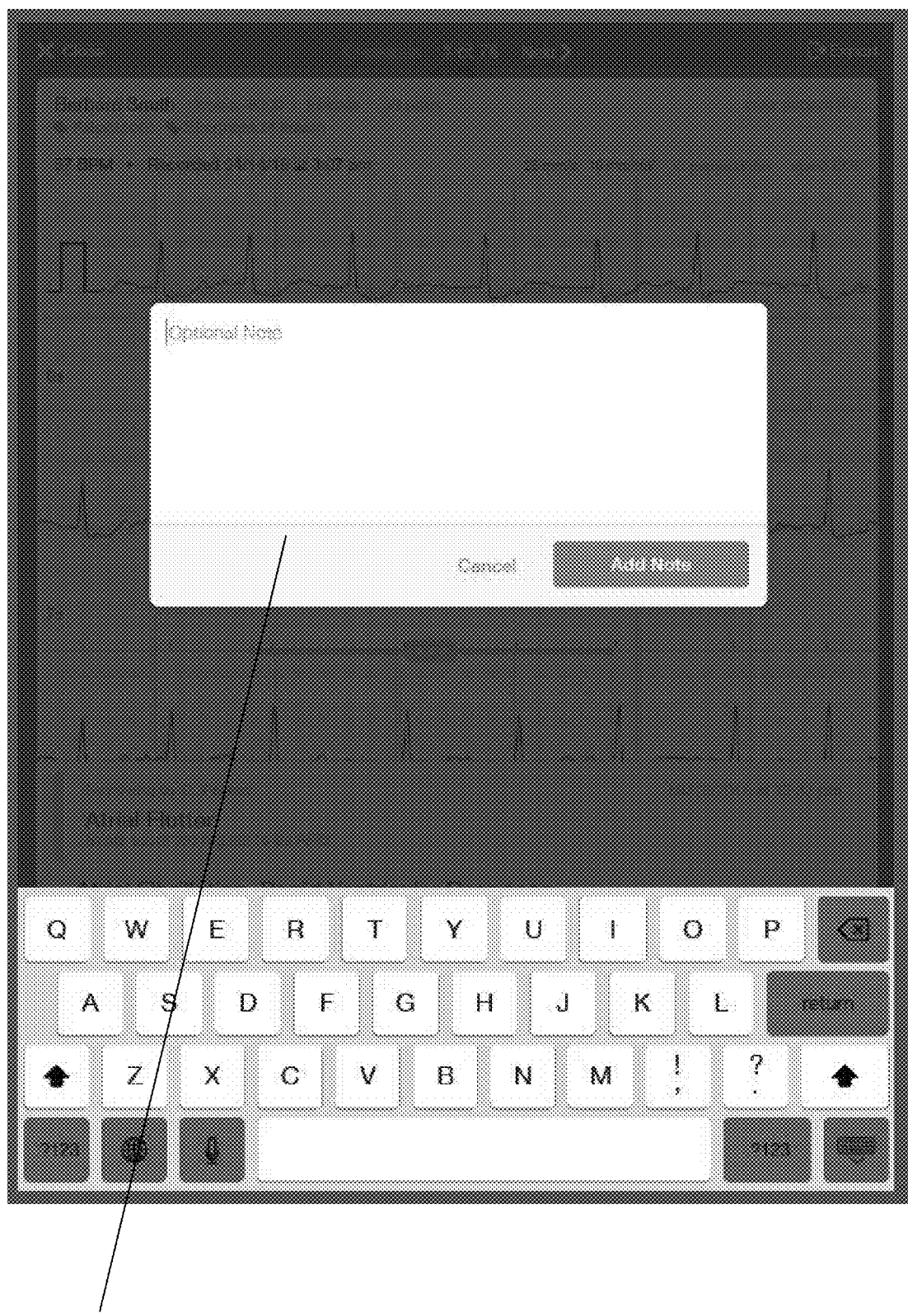
FIG. 9D shows a screenshot of an exemplary interface of a healthcare provider application that allows a healthcare provider to type in remarks relating to a received patient ECG.

In some embodiments of the healthcare provider application, the healthcare provider may also add an optional note to an ECG recording by selecting the "Add Optional Note" option 908 as illustrated by FIG. 9D. The healthcare provider application interface may provide for selection by the healthcare provider to adjust and/or select which types of status updates may be assigned to be notified. The software application interface may display the healthcare provider's total number of patients that are currently using the software application and have connected with the healthcare provider. An interface component provides for selection by the healthcare provider to add a new patient and send an invitation code via email. The healthcare provider may also send an electronic prescription for a cardiac health monitoring device or for regular cardiac health monitoring. The software application interface may display the healthcare provider's total number of patients that are currently pending acceptance of the healthcare provider's invitation to use the software application.

Notifications may not only be received by the healthcare provider, but they may also be sent by the healthcare provider to a patient of their choice. The notifications sent to patients may be automatically generated. The notifications sent to patients may be personalized push notifications that are automatically generated and sent to patients when patients complete a prescribed task. For example, a healthcare provider's software application may automatically generate and send a push notification to a patient congratulating a patient for achieving a prescribed task. Examples of prescribed tasks may be performing a physical activity, losing weight, decreasing BMI points, recording ECG data, and/or recording blood pressure measurements.

An additional interface of the healthcare provider's application may comprise a viewable, interactive patient directory or database. The patient directory or database may comprise a list of all patients that may be currently pending or may have accepted the healthcare provider's invitation to begin using the cardiac health monitoring software application. The patient directory may further display patient information such as name, phone number, age, gender, and an indication of whether or not they are connected and are using the cardiac health monitoring software application. Furthermore, the interface may also comprise a component to provide the healthcare provider with the option to electronically prescribe a cardiac health monitoring device and/or cardiac health monitoring. Such interface component may be placed in close proximity to the patient's name for ease of accessibility.

The interface may also comprise a component to provide the healthcare provider with the option to add a new patient. This interface component may be displayed in the patient directory interface of the software application. Upon selection by the healthcare provider, the "add new patient" interface component opens up a new interface. Such new interface may prompt the healthcare provider to enter potential new patient information such as patient medical record number, first name, last name, email address, mobile phone number, date of birth, and gender. Once the healthcare provider decides to add a new patient he or she may select the option to prescribe the cardiac health monitoring application as displayed on the interface. Moreover, once the cardiac health monitoring application is prescribed, the software application may automatically generate and send an email and a text message to the new patient instructing them on how to operate the cardiac health monitoring software application. The interface may also comprise a component to provide the healthcare provider with the option to select the length of time the healthcare provider monitors a patient and the amount of money charged per month to said patient. The automatically generated email may comprise an activation or referral code for the patient to use in order to obtain access to the software application.

An additional interface of the healthcare provider application may comprise an interactive interface to quickly view or scan relative distances between the R-R peaks in an ECG recording. The interface, in some embodiments, provides an array of R-R peak distances displayed by horizontal lines that the healthcare provider may interact with by clicking on each horizontal line. When the healthcare provider clicks on a horizontal line representing an R-R peak distance, the interface automatically zooms in on the segment of the ECG recording that corresponds to such R-R peak distance. In this manner, the interactive interface allows for the healthcare provider to quickly scan multiple R-R peak distances.

The platform, in some embodiments, provides different payment plans in order to obtain access to the disclosed software application. For example, a healthcare provider may purchase the software application, while a patient may purchase the health monitoring device associated with the software application, and the healthcare provider may bill the patient a recurrent fee for utilizing the software application. In some embodiments of the software applications, systems, devices, and methods described herein, a healthcare provider purchases the software application, while a patient purchases the health monitoring device associated with the software application, and the company selling the health monitoring device may bill the patient a recurrent fee for utilizing the software application. In some embodiments of the software applications, systems, devices, and methods described herein, an insurance company may offer a patient a free trial period wherein the patient may be offered the health monitoring device associated with the software application and the software application at no monetary charge for a specific time period; upon termination of said time period, the patient may elect to purchase the health monitoring device and the software application. The patient may be presented with the option to upgrade to a "Pro" or "Premium" membership plan wherein the patient may be charged a higher fee than the normal membership plan fee. The "Pro" or "Premium" plan may comprise access to a care plan. The care plan may comprise automatically- or healthcare provider-generated tasks for the patient to complete and reminders to complete such tasks. Such tasks may be based on the patient's current health status and may provide specific health goals to meet.

Billing Features

The platforms, devices, systems, and methods described herein, in some embodiments, provide payment and billing features for patients and healthcare providers. For example, a healthcare provider may purchase the platform, while a patient may purchase the health monitoring device associated with the platform, and the healthcare provider may bill the patient a recurrent fee for utilizing the platform. Some of the payment and billing features described herein, provide a healthcare provider the ability to purchase a platform (such as the platforms described herein), while a patient is provided the ability to purchase the health monitoring device having a platform incorporated therewith. In this embodiment, the company selling the health monitoring device may, for example, bill the patient a recurrent fee for utilizing the platform. In some embodiments of the platform of the payment and billing features, an insurance company offers a patient a free trial period wherein the patient may be offered the health monitoring device associated with the platform and the platform at no monetary charge for a specific time period; upon termination of said time period, the patient may elect to purchase the health monitoring device and the platform.

The platforms, devices, systems, and methods may include different types of payment and billing methods for patients and healthcare providers. For example, a healthcare provider may purchase the platform, while a patient may purchase the health monitoring device associated with the platform, and the healthcare provider may bill the patient a recurrent fee for utilizing the platform. In another aspect, a healthcare provider may purchase the platform, while a patient may purchase the health monitoring device associated with the platform, and the company selling the health monitoring device may bill the patient a recurrent fee for utilizing the platform. In some embodiments of the platform, an insurance company may offer a patient a free trial period wherein the patient may be offered the health monitoring device associated with the platform and the platform at no monetary charge for a specific time period; upon termination of said time period, the patient may elect to purchase the health monitoring device and the platform.

The patient may be presented with the option to upgrade to a "Pro" or "Premium" membership plan wherein the patient may be charged a higher fee than the normal membership plan fee. The "Pro" or "Premium" plan may comprise access to a care plan. The care plan platform interface may prompt a healthcare provider to automatically or manually generate tasks for the patient to complete. The platform may automatically generate reminders for the patient to complete such tasks. Such tasks may be based on the patient's current health status and may provide specific health goals to meet. The care plan interface may comprise the option to connect with family members via the platform, optionally alert the family members of the status of the patient's cardiac health, and optionally alert the family members of the status of the patient's task completions. The care plan platform may enable family members to automatically or manually send behavioral notifications to a patient upon successful completion of prescribed tasks such as correctly following a medication dosage regimen.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A system comprising:
   a sensor configured to:
      sense one or more physiological parameters of a user and generate physiological data based on the sensed one or more physiological parameters of the user; and
      transmit the physiological data;
   a first computing device configured to:
      receive the physiological data from the sensor;
      provide a first interface to display the physiological data; and
      transmit the physiological data; and
   a second computing device configured to:
      receive the physiological data from the first computing device;
      analyze the physiological data;
      generate, based on the analysis, a healthcare provider communication comprising results of the analysis of the physiological data; and
      transmit the healthcare provider communication to the first computing device, wherein the first computing device and the second computing device include a patient module and a healthcare provider module respectively which form a software platform via which the physiological data and the healthcare provider communication are exchanged.

2. The system of claim 1, wherein the healthcare provider application comprises a database including physiological data sensed from a plurality of users and wherein to analyze the physiological data, the second computing device is configured to generate a risk score for the user based on the physiological data and the physiological data sensed from the plurality of users.

3. The system of claim 1, wherein the first computing device is further to:
   receive the healthcare provider communication; and
   provide a second interface to display the healthcare provider communication.

4. The system of claim 1, wherein the first computing device is further to:

provide a second interface to initiate measurement of the physiological parameter; and in response to receiving via the second interface, an indication that the user wishes to initiate measurement of the physiological parameter, transmit an instruction to the sensor to initiate measurement of the physiological parameter.

5. The system of claim 4, wherein the second interface comprises an interactable representation of each of a plurality of physiological parameters, and wherein to receive the indication, the first computing device is to detect an interaction with one of the plurality of interactable representations.

6. The system of claim 5, wherein the instruction indicates the physiological parameter as a physiological parameter corresponding to the one of the plurality of interactable representations.

7. The system of claim 4, wherein the first computing device is further to:

in response to receiving via the second interface, an indication that the user wishes to initiate measurement of the physiological parameter, provide a third interface that displays instructions for attaching the sensor to a body of the user.

8. The system of claim 1, wherein the physiological parameter comprises an electrocardiogram (EKG) of the user.

9. The system of claim 1, wherein the physiological parameter comprises a resting heart rate of the user.

10. The system of claim 1, wherein the sensor is configured to operably couple with the first computing device.

11. A method comprising:

sensing, via a sensor, one or more physiological parameters of a user and generating physiological data based on the sensed one or more physiological parameters of the user;

transmitting the physiological data to a first computing device;

providing, via the first computing device, a first interface to display the physiological data;

transmitting the physiological data to a second computing device;

analyzing, by the second computing device, the physiological data;

generating, based on the analysis, a healthcare provider communication comprising results of the analysis of the physiological data; and transmitting the healthcare provider communication to the first computing device, wherein the first computing device and the second computing device include a patient module and a healthcare provider module respectively which form a software platform via which the physiological data and the healthcare provider communication are exchanged.

12. The method of claim 11, wherein the healthcare provider application comprises a database including physiological data sensed from a plurality of users and wherein analyzing the physiological comprises generating a risk score for the user based on the physiological data and the physiological data sensed from the plurality of users.

13. The method of claim 11, further comprising:

Receiving at the first computing device, the healthcare provider communication; and providing a second interface to display the healthcare provider communication.

14. The method of claim 11, further comprising:

providing a second interface to initiate measurement of the physiological parameter; and in response to receiving via the second interface, an indication that the user wishes to initiate measurement of the physiological parameter, transmitting an instruction to the sensor to initiate measurement of the physiological parameter.

15. The method of claim 14, wherein the second interface comprises an interactable representation of each of a plurality of physiological parameters, and wherein receiving the indication comprises detecting an interaction with one of the plurality of interactable representations.

16. The method of claim 15, wherein the instruction indicates the physiological parameter as a physiological parameter corresponding to the one of the plurality of interactable representations.

17. The method of claim 14, further comprising:

in response to receiving via the second interface, an indication that the user wishes to initiate measurement of the physiological parameter, providing a third interface that displays instructions for attaching the sensor to a body of the user.

18. The method of claim 11, wherein the physiological parameter comprises an electrocardiogram (EKG) of the user.

19. The method of claim 11, wherein the physiological parameter comprises a resting heart rate of the user.

20. The method of claim 11, wherein the sensor is configured to operably couple with the first computing device.

* * * * *